(12) United States Patent
Usui et al.

(10) Patent No.: US 11,062,814 B1
(45) Date of Patent: Jul. 13, 2021

(54) BOX-TYPE STRUCTURE HAVING SHIELDING FUNCTION

(71) Applicant: Nippon Light Metal Company, Ltd., Tokyo (JP)

(72) Inventors: Hideaki Usui, Tokyo (JP); Hidaka Furuya, Tokyo (JP); Maki Takahashi, Tokyo (JP); Hidenori Ishikawa, Tokyo (JP)

(73) Assignee: Nippon Light Metal Company, Ltd., Tokyo (JP)

( * ) Notice: Subject to any disclaimer, the term of this patent is extended or adjusted under 35 U.S.C. 154(b) by 0 days.

(21) Appl. No.: 16/755,532

(22) PCT Filed: Oct. 11, 2018

(86) PCT No.: PCT/JP2018/038005
§ 371 (c)(1),
(2) Date: Apr. 10, 2020

(87) PCT Pub. No.: WO2019/074078
PCT Pub. Date: Apr. 18, 2019

(30) Foreign Application Priority Data

Oct. 11, 2017 (JP) .............................. JP2017-198061

(51) Int. Cl.
| | | |
|---|---|---|
| G21F 1/08 | (2006.01) | |
| A61B 6/00 | (2006.01) | |
| A61N 5/10 | (2006.01) | |
| G21F 3/00 | (2006.01) | |
| A61B 6/10 | (2006.01) | |

(52) U.S. Cl.
CPC ............... *G21F 1/08* (2013.01); *A61B 6/107* (2013.01); *A61B 6/508* (2013.01); *A61N 5/1077* (2013.01); *G21F 3/00* (2013.01); *A61N 2005/109* (2013.01); *A61N 2005/1094* (2013.01)

(58) Field of Classification Search
USPC ...................................................... 250/518.1
See application file for complete search history.

(56) References Cited

U.S. PATENT DOCUMENTS

| | | | | |
|---|---|---|---|---|
| 3,426,197 | A | 2/1969 | Waly et al. | |
| 3,452,197 | A * | 6/1969 | Childers | G01T 3/06 250/392 |
| 7,714,297 | B2 * | 5/2010 | Morris | G01V 5/0025 250/393 |
| 8,710,476 | B2 * | 4/2014 | Eckhoff | A61B 6/107 250/505.1 |
| 10,458,930 | B2 * | 10/2019 | Torbert, III | G01N 33/24 |
| 10,877,165 | B2 * | 12/2020 | Usui | G21F 5/06 |
| 2013/0020512 | A1 | 1/2013 | Roy | |
| 2013/0112898 | A1 | 5/2013 | Eckhoff et al. | |
| 2014/0265057 | A1 | 9/2014 | Park et al. | |
| 2016/0284430 | A1 | 9/2016 | Sane et al. | |
| 2017/0052265 | A1 | 2/2017 | Fukuda et al. | |

FOREIGN PATENT DOCUMENTS

| | | |
|---|---|---|
| CN | 101302367 B | 3/2011 |
| CN | 104744945 A | 7/2015 |
| CN | 104228268 B | 5/2016 |
| CN | 205987231 U | 2/2017 |
| EP | 3407092 A1 | 11/2018 |
| JP | S51-94098 A | 8/1976 |
| JP | H 08-201581 A | 8/1996 |
| JP | 2004-094706 A | 3/2004 |
| JP | 2004-233168 A | 8/2004 |
| JP | 2014-092462 A | 5/2014 |
| JP | 2016-211968 A | 12/2016 |
| JP | 2017-125828 A | 7/2017 |
| RU | 2591207 C1 | 7/2016 |

OTHER PUBLICATIONS

Notice of Reasons for Rejection issued to TW Application No. TW107135853, dated Mar. 20, 2019.
Notice of Reasons for Rejection issued to TW Application No. TW107135854, dated Aug. 5, 2019.
International Search Report in PCT/JP2018/038005 dated Dec. 25, 2018.
Written Opinion in PCT/JP2018/038005 dated Dec. 17, 2018.
Extended European Search Report issued in European Patent Application No. 18865891.8, dated Oct. 8, 2020.
Extended European Search Report issued in the European Patent Application No. 18867050.9, dated Oct. 8, 2020.
Office Action issued in Russian Patent Application No. 2020115473, dated Nov. 19, 2020.
Office Action issued in Russian Patent Application No. 2020115474, dated Nov. 19, 2020.
Notification of Reasons for Refusal issued in Japanese Patent Application No. 2019-548247, dated Apr. 20, 2021.

* cited by examiner

*Primary Examiner* — Phillip A Johnston
(74) *Attorney, Agent, or Firm* — Knobbe Martens Olson & Bear LLP

(57) ABSTRACT

A box-type structure includes a structure having neutron beam shielding performance. It is possible to accommodate an organism to be irradiated in the structure. The box-type structure includes shielding plates, which include a lithium-fluoride sintered body having neutron shielding performance. Edge portions of the shielding plates are joined by abutting against one another. The edge portions of the shielding plates have a halving joint structure, and the halving joint structure has a stepped or inclined cutout shape. The box-type structure has a plurality of surfaces, and at least one of the faces may be removable or there may be an opening portion in part of the surface.

6 Claims, 16 Drawing Sheets

PLAN VIEW

A-A CROSS-SECTIONAL VIEW

B-B CROSS-SECTIONAL VIEW

PLAN VIEW

A-A CROSS-SECTIONAL VIEW

B-B CROSS-SECTIONAL VIEW

PLAN VIEW

A-A CROSS-SECTIONAL VIEW

B-B CROSS-SECTIONAL VIEW

PLAN VIEW

A-A CROSS-SECTIONAL VIEW

B-B CROSS-SECTIONAL VIEW

PLAN VIEW

A-A CROSS-SECTIONAL VIEW

B-B CROSS-SECTIONAL VIEW

PLAN VIEW

A-A CROSS-SECTIONAL VIEW

B-B CROSS-SECTIONAL VIEW

FRONT VIEW

RIGHT-SIDE VIEW

A-A CROSS-SECTIONAL VIEW

B-B CROSS-SECTIONAL VIEW

C-C CROSS-SECTIONAL VIEW

FRONT VIEW

PLAN VIEW

RIGHT-SIDE VIEW

A-A CROSS-SECTIONAL VIEW

B-B CROSS-SECTIONAL VIEW

C-C CROSS-SECTIONAL VIEW

BOX-TYPE STRUCTURE HAVING SHIELDING FUNCTION

This application is the U.S. National Phase under 35 U.S.C. § 371 of International Application No. PCT/JP2018/038005, filed Oct. 11, 2018, designating the U.S., which claims priority to Japanese Application No. JP 2017-198061, filed Oct. 11, 2017, the entire contents of which are incorporated herein by reference.

TECHNICAL FIELD

The present invention relates to a box-type structure having a neutron-shielding function.

BACKGROUND ART

In recent years, research and development of boron-neutron capture therapy (BNCT) is rapidly progressing as a means of cancer treatment. Boron-neutron capture therapy is radiotherapy which uses a neutron beam. First, a boron compound that is specifically taken in by cancer cells is administered to a patient. Subsequently, the cancer cells in which the boron compound has accumulated are irradiated with a neutron beam whose energy is controlled within a predetermined range. When the neutron beam collides with the boron compound, α rays are generated. The cancer cells are killed by the α rays.

Boron-neutron capture therapy is promising as a means of treating cancer and is moving into the clinical trial phase. The neutron irradiation apparatus used in boron-neutron capture therapy brings about therapeutic effects by using a thermal neutron beam or an epithermal neutron beam. The neutron irradiation environment is a field where radioactive rays having energies in a certain range coexist.

It has been necessary so far to use a nuclear reactor as a neutron generator for supplying a neutron beam to a neutron irradiation apparatus. However, in recent years, small neutron generators to be installed in hospitals are being proposed. In such a small neutron generator, protons and deuterons accelerated by an accelerator collide with a beryllium or lithium target. The generated neutron beam has a higher proportion of thermal neutrons and epithermal neutrons than those generated in conventional equipment. The generated neutron beam is then decelerated by a moderator to provide a neutron beam irradiation environment having little influence on human bodies.

When neutrons are irradiated in neutron capture therapy, it is necessary to provide a neutron-shielding means to irradiate a specific site. In order to examine the effects of neutron capture therapy, experiments of irradiating small animals, such as mice, with neutrons have been performed. Patent Document 1 relates to a case of applying neutron capture therapy using a shielding plate of lithium fluoride to mammals other than human beings. The object thereof is to minimize neutrons given to normal tissue when the target site is deep inside the irradiation object, and to provide sufficient neutrons to the target located deep inside the irradiation object by suppressing the reduction in depth and reachability of neutrons going into the body.

Patent Document 1: Japanese Unexamined Patent Application, Publication No. 2004-233168

DISCLOSURE OF THE INVENTION

Problems to be Solved by the Invention

However, in these shielding methods, the installability and shielding properties of a shield body may be restricted by the shape of the organism which is to be an irradiation object, as well as the size of the irradiation site. Accordingly, there is required a shielding means that three-dimensionally shields the irradiation object and separates an irradiation region of the neutron beam from a non-irradiation region by means of a simple structure.

Thus, it is an object of the present invention to provide a box-type structure that has a simple structure having neutron beam-shielding performance and can accommodate an organism which is to be an irradiation target.

Means for Solving the Problems

The present inventors have considered how to solve the above-described problems. As a result, the present inventors have found that a box-type structure accommodating an organism can be easily produced by configuring the box-type structure using shielding plates made of a specific material and having a neutron-shielding function, and by making the joining structure at the edge portions of the shielding plates firm, and thus have accomplished the present invention. The present invention provides the following.

(1) The present invention relates to a box-type structure including a plurality of shielding plates containing lithium fluoride and having neutron-shielding performance, wherein edge portions of the shielding plates are abutted and joined to each other.

(2) The present invention relates to the box-type structure according to aspect (1), wherein the edge portions of the shielding plates have a halving joint structure, and the halving joint structure has a stepped or inclined cutout shape.

(3) The present invention relates to the box-type structure according to aspect (1) or (2), wherein the box-type structure has a plurality of faces, and at least one of the faces is removable.

(4) The present invention relates to the box-type structure according to any one of aspects (1) to (3), wherein a part of the faces of the box-type structure has an opening portion.

(5) The present invention relates to the box-type structure according to any one of aspects (1) to (4), wherein the shielding plates are joined with adhesive tape.

(6) The present invention relates to the box-type structure according to any one of aspects (1) to (4), wherein the edge portions of the shielding plates are joined via an adhesive.

Effects of the Invention

According to the present invention, in the box-type structure having neutron-shielding performance, since a plurality of shielding plates having neutron-shielding performance are joined in combination, a simple three-dimensional structure can be obtained. The size of the box-type structure can be freely adjusted according to the size and the number of the combined shielding plates.

In addition, the edge portions of the neutron-shielding plates can be easily joined to each other by providing stepped or inclined halving joint structures at the edge portions, and thus an effect of stabilizing the joining structure can be obtained.

It is possible to accommodate an organism or the like in a space shielded from a neutron beam and perform a test in a state in which not all of the organism or the like is irradiated with a neutron beam. Furthermore, when the box-type structure has a partly open structure, a part of the organism or the like can be taken outside of the shielding region and can be irradiated with a neutron beam in only that part, broadening the application range of a neutron beam's irradiation objects and test conditions.

This box-type structure is suitable for the field of radiating a neutron beam and examining its action and influence. It can be used in a test using a small animal such as a mouse, or in an irradiation test relating to radiotherapy, etc. In addition, a plurality of irradiation bodies can be simultaneously irradiated by providing, for example, partitions on the inside of the box-type structure or by providing a plurality of the box-type structures, which improves the efficiency of the irradiation test.

PREFERRED MODE FOR CARRYING OUT THE INVENTION

Embodiments of the box-type structure according to the present invention will now be described. The present invention is not limited to the following embodiments and can be implemented by being appropriately modified within a range that does not deviate from the gist of the present invention.

(Box-Type Structure)

The box-type structure includes a plurality of shielding plates containing lithium fluoride and having neutron-shielding performance. Edge portions of the shielding plates are abutted and joined to each other. Here, the term "neutron-shielding performance" refers to performance of shielding neutron beams. In the present specification, "neutron-shielding" may be described as "neutron beam-shielding". The shielding plate according to the present invention means a neutron-shielding plate. The box-type structure is composed of a plurality of shielding plates having neutron-shielding performance assembled into a box-like shape, and has a simple three-dimensional structure.

Figure 1:
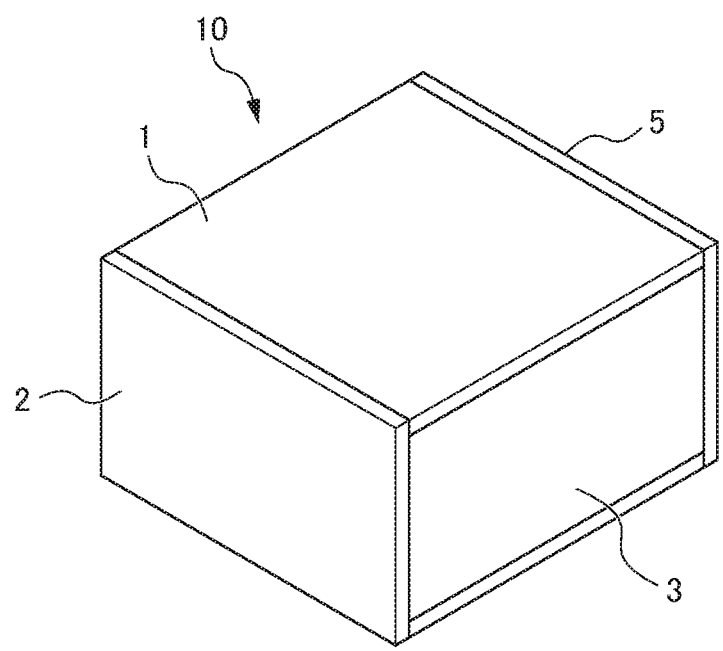
FIG. 1 is a schematic view illustrating a box-type structure according to an embodiment of the present invention.

The external appearance of the box-type structure is shown in FIG. 1. Six shielding plates, e.g., shielding plates 1 and 2, are assembled to make the box-type structure 10. The edge portion of the shielding plates are abutted on each other such that the end faces are closely joined to each other. As the joining means, adhesive tape or an adhesive can be used. The box-type structure shown in FIG. 1 is an embodiment in which all outer faces are surrounded by shielding plates.

Figure 2A:
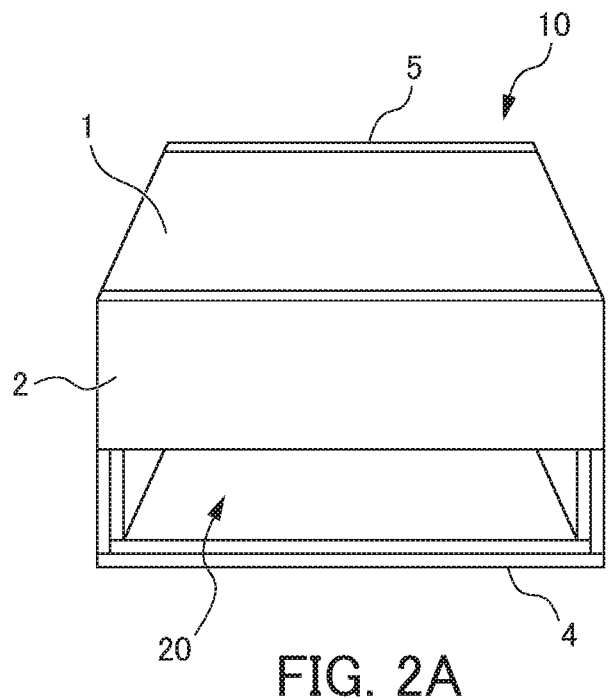
FIG. 2 includes schematic views illustrating a box-type structure according to another embodiment of the present invention. (a) is a front view, and (b) is a perspective view.
Figure 2B:
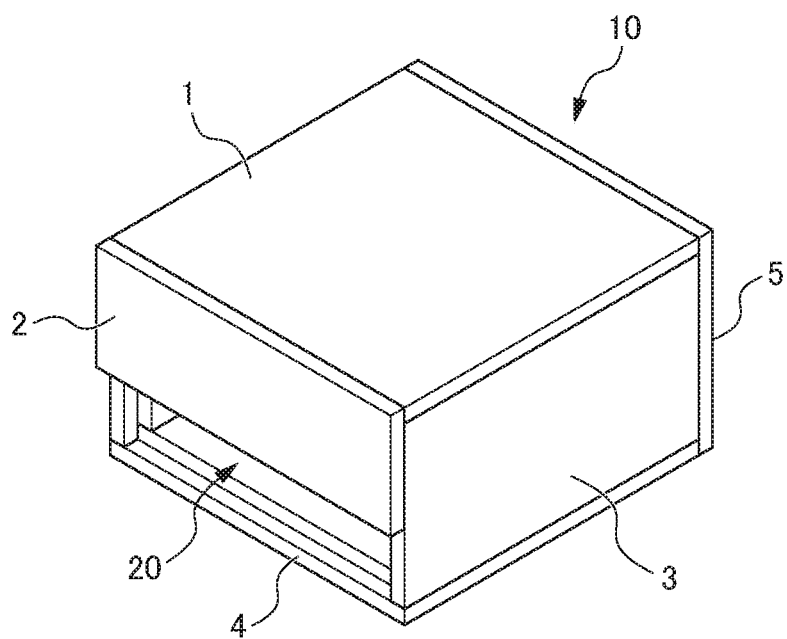

The box-type structure 10 shown by (a) and (b) in FIG. 2 is another embodiment having an opening 20 provided in a part of the outer faces. Six shielding plates, e.g., shielding plates, 1, 2, 3, and 4, are assembled to make the box-type structure. The edge portions of the shielding plates are abutted on each other such that the end faces of the shielding plates are closely joined to each other. As shown by (a) and (b) in FIG. 2, a part of the sides of the shield 2 is short in length such that the opening 20 is formed at that part.

The shielding plates of the box-type structure are made of a material containing lithium fluoride (LiF), which is excellent in its neutron-shielding performance. The shielding plates of the box-type structure prevent the neutron beam radiated from the outside from passing through. Accordingly, the shielding plates reduce the neutron beams that reach the inside of the box-type structure, and thus can make a region (non-irradiation region) that is not substantially irradiated with the neutron beam in the box-type structure.

The box-type structure has a three-dimensional shape, such as a cube or a rectangular parallelepiped, which forms a three-dimensional neutron beam-shielding space. The shielding space can accommodate a small animal, even if it has a certain volume or more.

Since the edge portions of the shielding plates are abutted on and joined to each other, the edge portions form a joining structure in which the end faces are closely joined to each other. Accordingly, the neutron beam is sufficiently prevented from passing through the gap between the edge portions, which can form a neutron beam-shielding space inside the box-type structure.

(Shielding Plate)

The shielding plate has a halving joint structure at the edge portion. The halving joint structure refers to a structure which includes a concave portion (hereinafter, referred to as "concave") or a convex portion (hereinafter, referred to as "convex") at the edge portions of the shielding plates in such a manner that the concave and the convex can make a close fit. In the present specification, the portion having a halving joint structure in an edge portion of the shielding plate may be also referred to as the "halving joint portion". The method for forming a halving joint structure at an edge portion of a shielding plate is referred to as "halving joint processing".

Figure 3A:
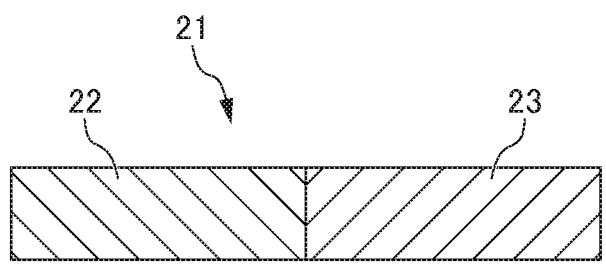
FIG. 3 includes schematic views for explaining halving joint structures at edge portions of shielding plates. (a) is a view illustrating a halving joint structure composed of edge portions of shielding plates having stepped concave and convex portions. (b) is a view illustrating a halving joint structure composed of edge portions of shielding plates having inclined concave and convex portions. (c) is a view illustrating a structure composed of flat edge portions of shielding plates abutted against each other.
Figure 3B:
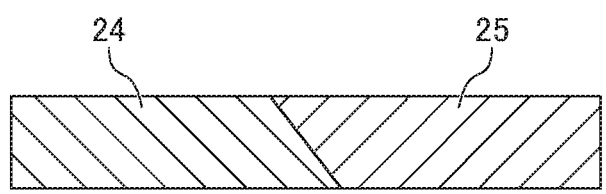
Figure 3C:
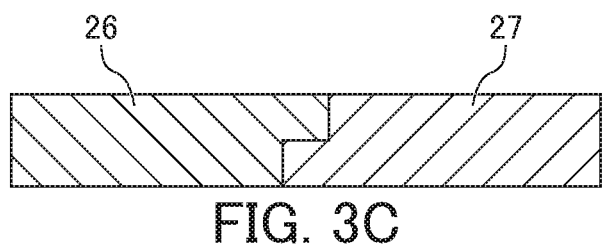
Figure 4A:
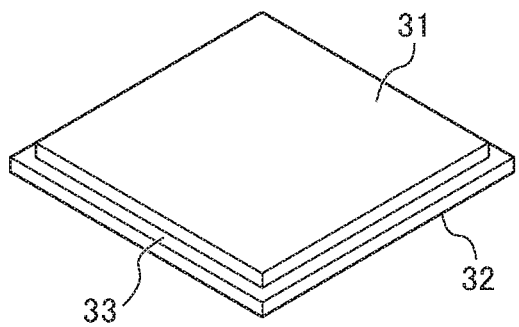
FIG. 4 includes views illustrating an exemplary form of the edge portion of a shielding plate having a halving joint structure. (a) is a perspective view, (b) is a plan view, (c) is a cross-sectional view along the line A-A, and (d) is a cross-sectional view along the line B-B.
Figure 4B:
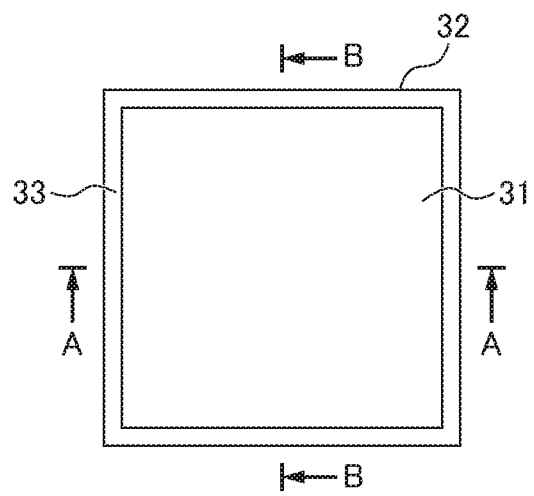
Figure 4C:
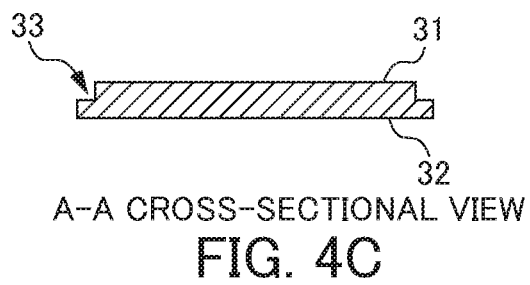
Figure 4D:
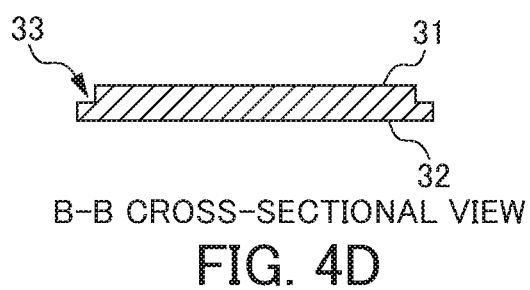
Figure 5A:
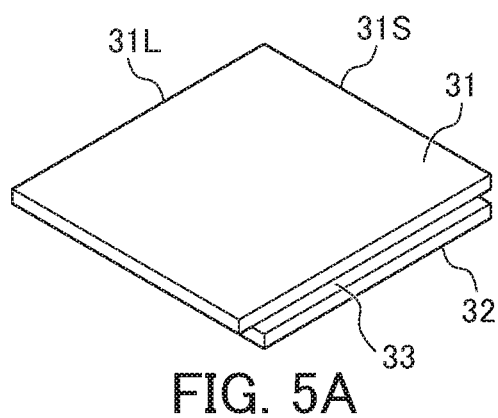
FIG. 5 includes views illustrating another exemplary form of the edge portion of a shielding plate having a halving joint structure. (a) is a perspective view, (b) is a plan view, (c) is a cross-sectional view along the line A-A, and (d) is a cross-sectional view along the line B-B.
Figure 5B:
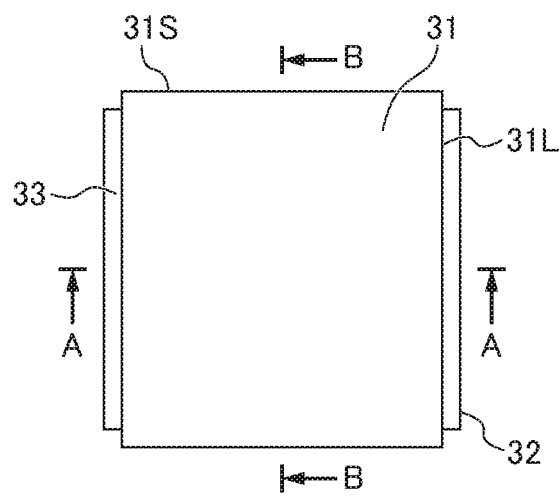
Figure 5C:
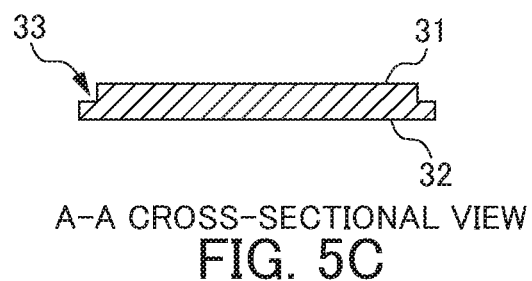
Figure 5D:
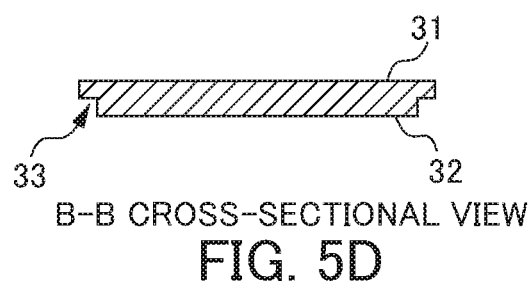
Figure 5E:
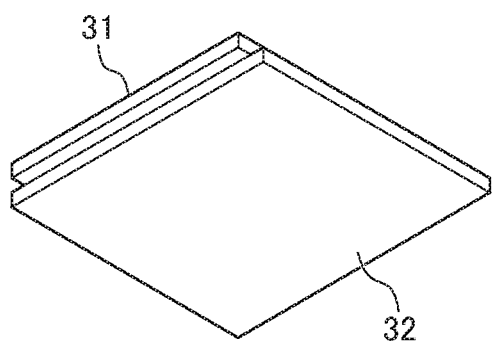
Figure 6A:
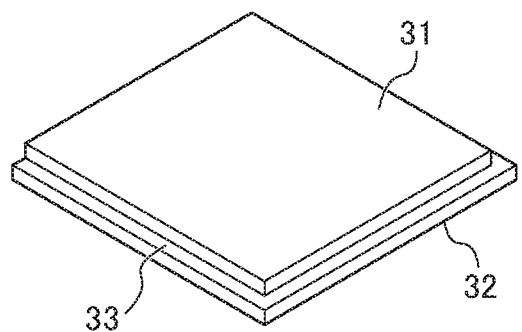
FIG. 6 includes views illustrating another exemplary form of an edge portion of a shielding plate having a halving joint structure. (a) is a perspective view, (b) is a plan view, (c) is a cross-sectional view along the line A-A, and (d) is a cross-sectional view along the line B-B.
Figure 6B:
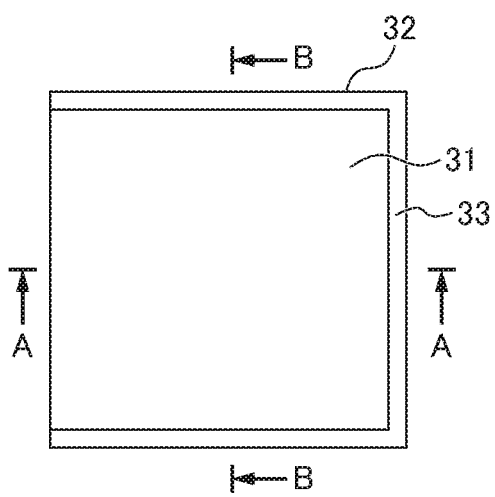
Figure 6C:
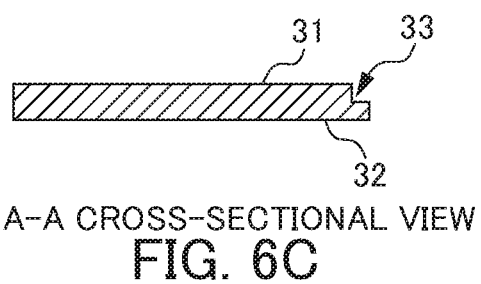
Figure 6D:
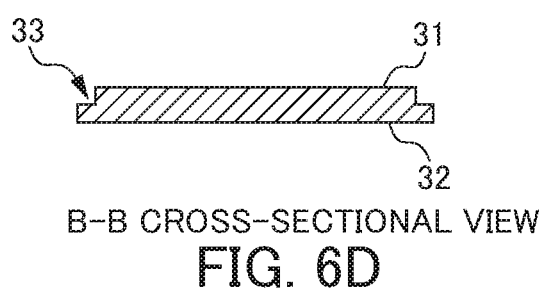
Figure 7A:
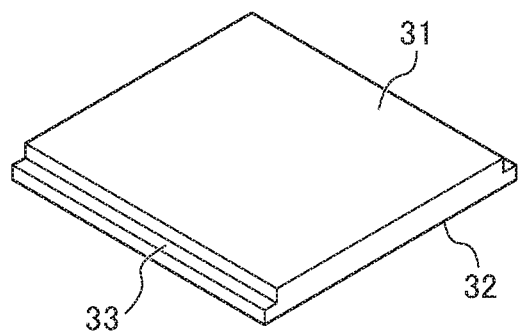
FIG. 7 includes views illustrating another exemplary form of an edge portion of a shielding plate having a halving joint structure. (a) is a perspective view, (b) is a plan view, (c) is a cross-sectional view along the line A-A, and (d) is a cross-sectional view along the line B-B.
Figure 7B:
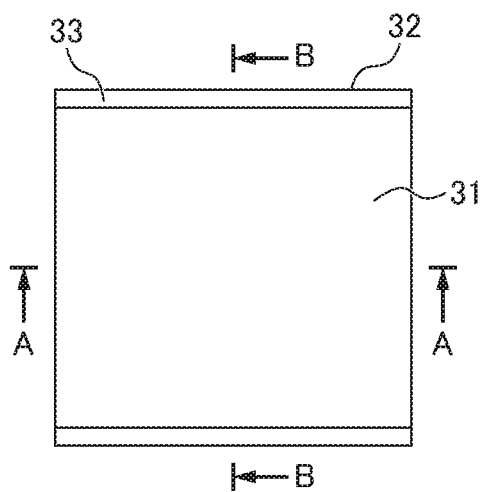
Figure 7C:
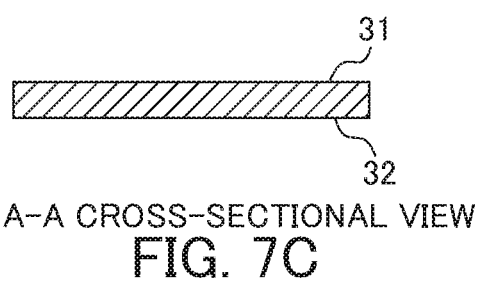
Figure 7D:
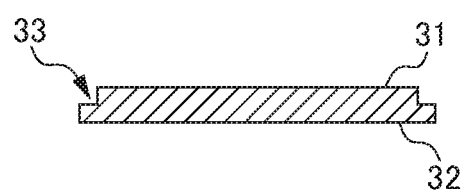
Figure 8A:
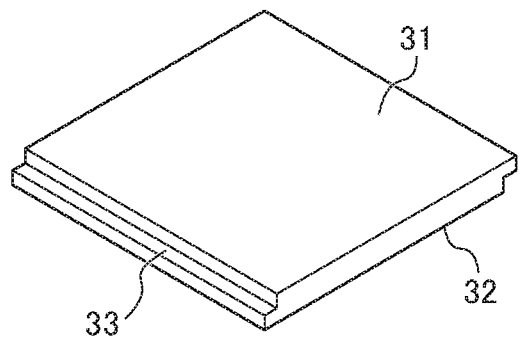
FIG. 8 includes views illustrating another exemplary form of an edge portion of a shielding plate having a halving joint structure. (a) is a perspective view, (b) is a plan view, (c) is a cross-sectional view along the line A-A, and (d) is a cross-sectional view along the line B-B.
Figure 8B:
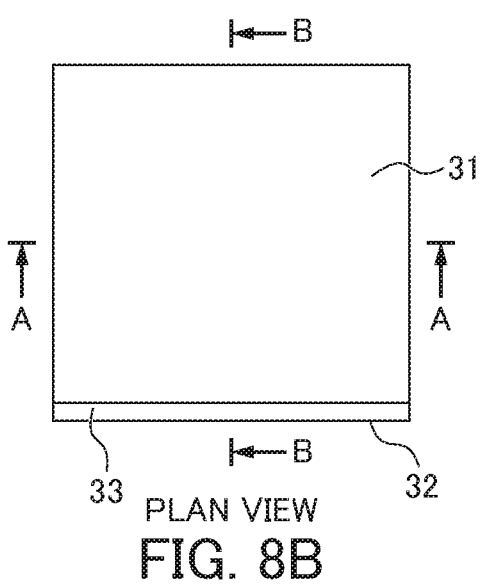
Figure 8C:
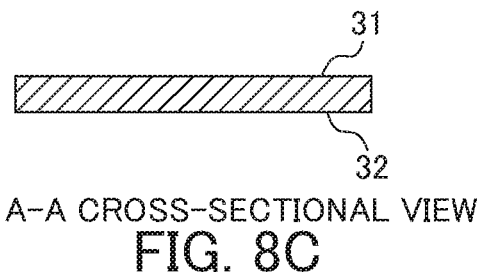
Figure 8D:
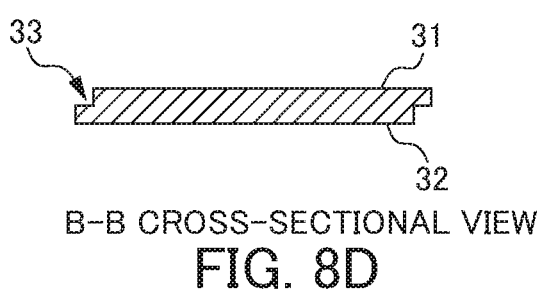
Figure 9A:
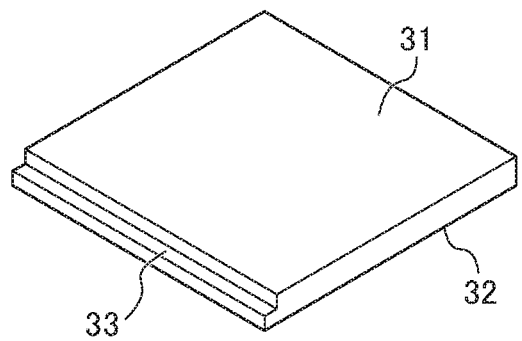
FIG. 9 includes views illustrating another exemplary form of an edge portion of a shielding plate having a halving joint structure. (a) is a perspective view, (b) is a plan view, (c) is a cross-sectional view along the line A-A, and (d) is a cross-sectional view along the line B-B.
Figure 9B:
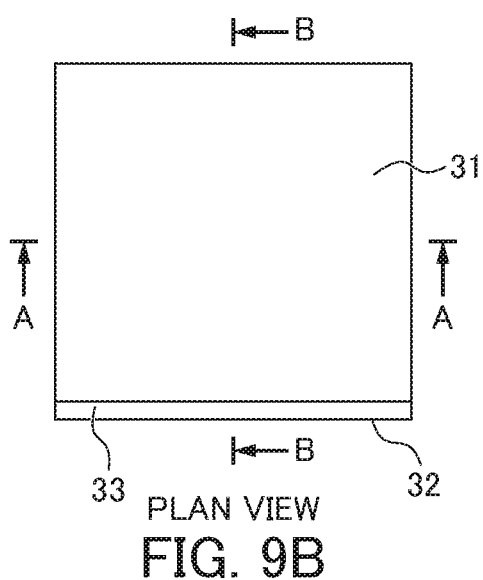
Figure 9C:
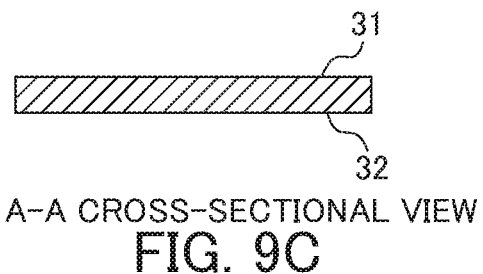
Figure 9D:
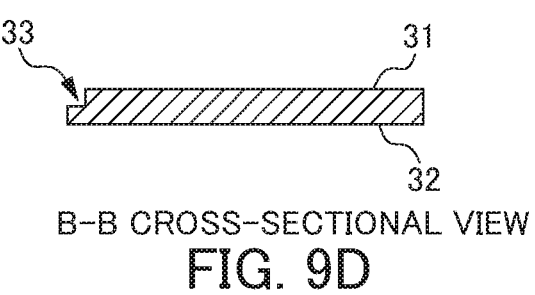
Figure 10A:
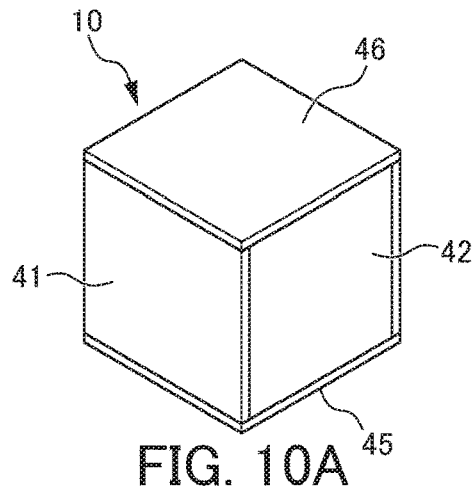
FIG. 10 includes views illustrating another embodiment related to the box-type structure. (a) is a perspective view, (b) is a front view, (c) is a right-side view. (d) is a cross-sectional view along the line A-A, (e) is a cross-sectional view along the line B-B, (f) is a cross-sectional view along the line C-C, and (g) is a view illustrating the internal structure.
Figure 10B:
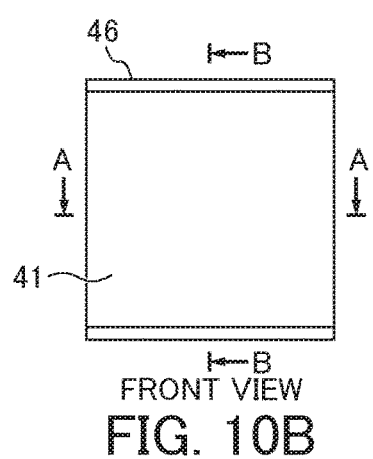
Figure 10C:
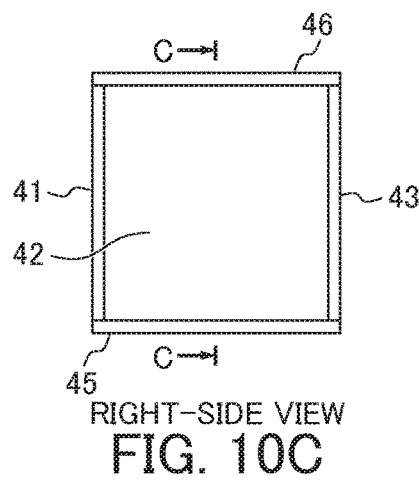
Figure 10D:
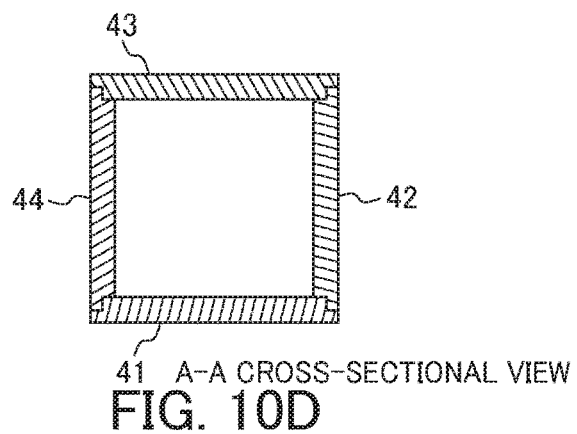
Figure 10E:
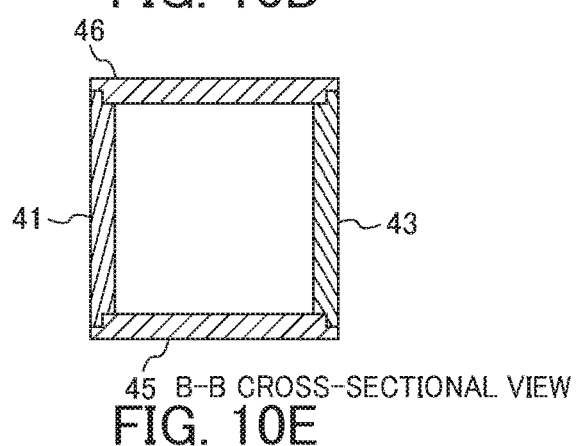
Figure 10F:
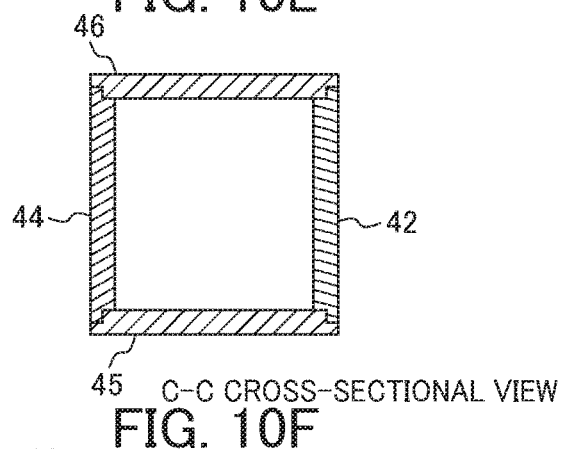
Figure 10G:
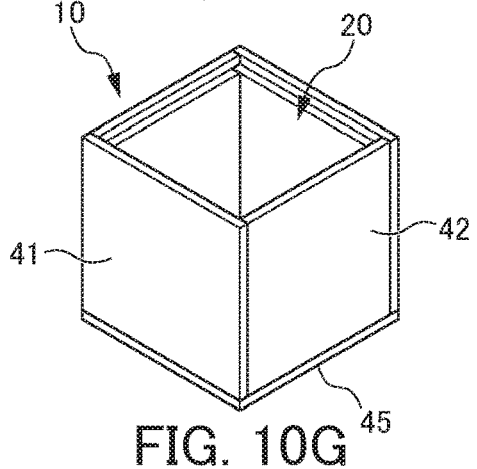
Figure 11A:
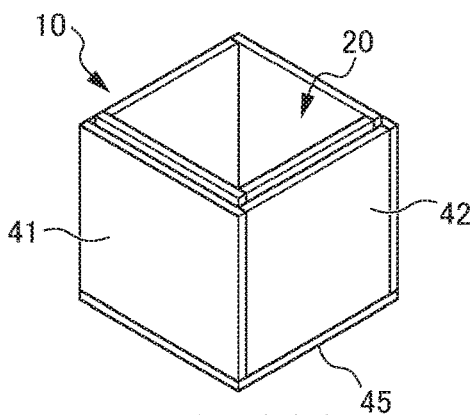
FIG. 11 includes views illustrating an embodiment related to the box-type structure. (a) is a perspective view, (b) is a perspective view from another direction, (c) is a front view, (d) is a plan view, (e) is a right-side view. (f) is a cross-sectional view along the line A-A, (g) is a cross-sectional view along the line B-B, and (h) is a cross-sectional view along the line C-C.
Figure 11B:
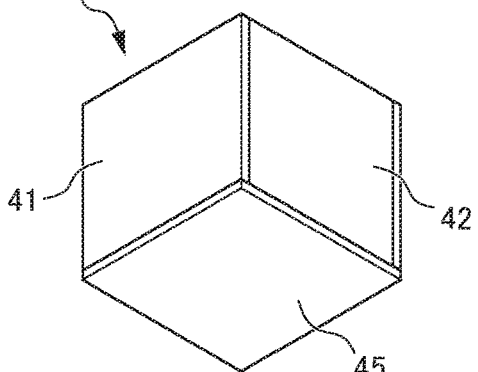
Figure 11C:
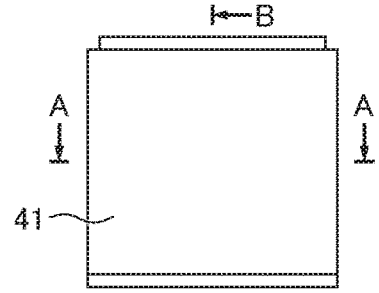
Figure 11D:
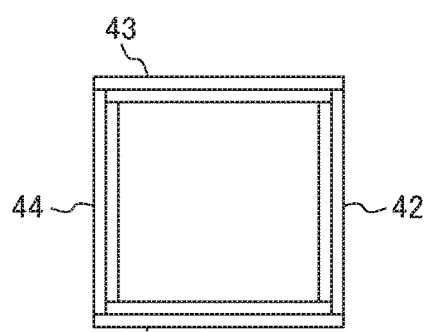
Figure 11E:
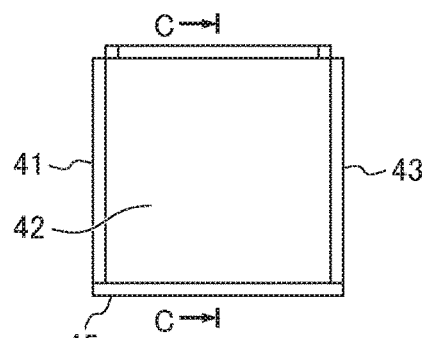
Figure 11F:
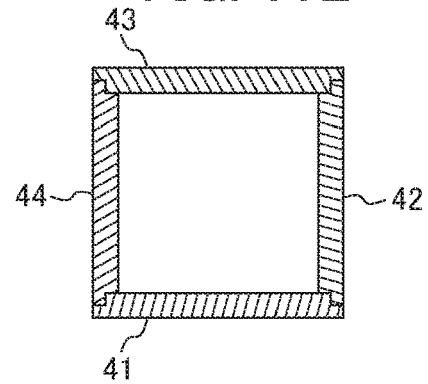
Figure 11G:
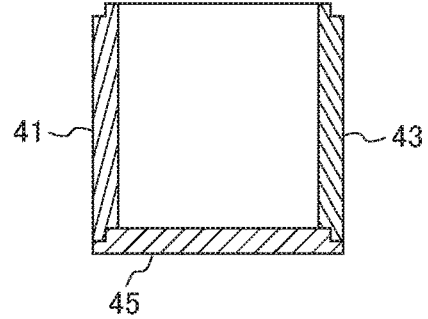
Figure 11H:
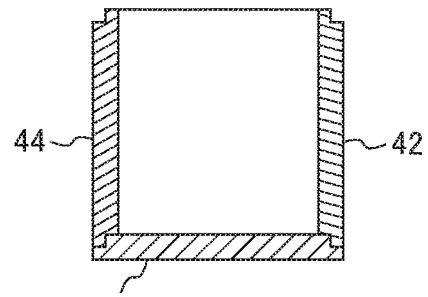

The outline of the halving joint structure will be described using an example shown by (a) and (b) in FIG. 3. (a) in FIG. 3 shows an exemplary form having stepped concave and convex portions at edge portions of shielding plates. (b) in FIG. 3 shows an exemplary form having inclined concave and convex portions at edge portions of shielding plates.

As shown in (a) of FIG. 3, when the edge portion of one shielding plate 22 includes a halving joint portion having a concave (or convex) portion and the edge portion of the other shielding plate 23 includes a halving joint portion having a convex (or concave) portion, the concave and convex portions make a close fit by abutting the edge portions of the shielding plates to give a joining structure 21 in which the end faces of the shielding plates 22 and 23 are closely joined to each other. In the halving joint structure of the present embodiment, the concave and convex portions at the edge portions of the shielding plates preferably have a stepped cutout shape as shown by (a) in FIG. 3 or an inclined cutout shape as shown by (b) in FIG. 3. Regarding the halving joint structure, there are various exemplary forms as shown in FIGS. 4 to 9.

Figure 17A:
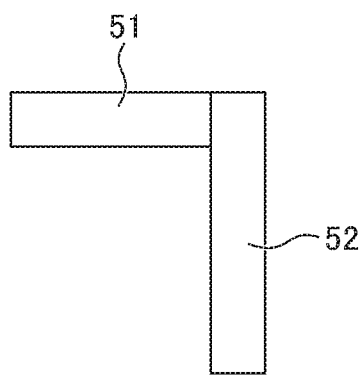
FIG. 17 includes schematic views illustrating cross-sections of structures composed of edge portions of shielding plates abutted against each other. (a) is a view illustrating a structure formed of stepped concave and convex portions. (b) is a view illustrating a structure formed of inclined concave and convex portions. (c) is a view illustrating a structure formed of flat edge portions.
Figure 17B:
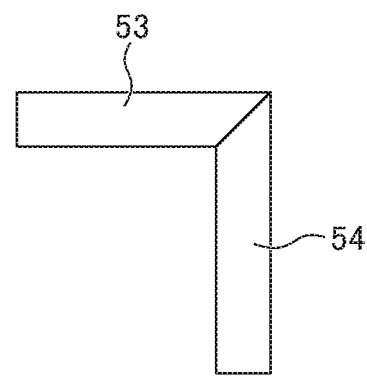
Figure 17C:
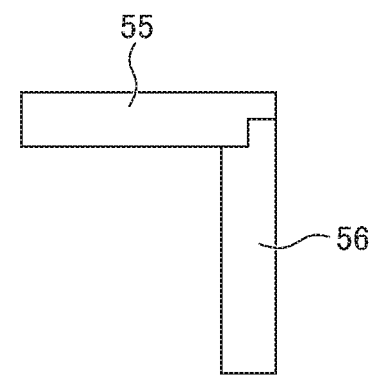

As shown by (c) in FIG. 3, when the edge portions are joined to each other through flat faces and not by a halving joint structure, the neutron-shielding properties may decrease compared to the case using halving joint structures such as those shown by (a) or (b) in FIG. 3. However, supplement firm engagement and sufficient shielding performance can be made by fixing the joining faces of the edge portions with an adhesive containing lithium fluoride. In addition, (a) to (c) in FIG. 17 show exemplary forms in which these shielding plates are joined for the application to box-type structures. (a) in FIG. 17 is a view illustrating a structure composed of stepped concave and convex portions, (b) in FIG. 17 is a view illustrating a structure composed of inclined concave and convex portions, and (c) in FIG. 17 is a view illustrating a structure composed of flat edge portions.

(a) to (d) in FIG. 4 are views illustrating exemplary forms in which the edge portions of the shielding plates have halving joint structures. (a) in FIG. 4 is a perspective view, (b) in FIG. 4 is a plan view, (c) in FIG. 4 is a cross-sectional view along the line A-A, and (d) in FIG. 4 is a cross-sectional view along the line B-B. FIGS. 5 to 9 show other exemplary forms of shielding plates. In each figure, similar to (a) to (d) of FIG. 4, (a) is a perspective view, (b) is a plan view, (c) is a cross-sectional view along the line A-A, and (d) is a cross-sectional view along the line B-B.

FIG. 4 shows an example in which four sides of a shielding plate have stepped halving joint structures. As understood from the cross-sectional views shown by (c) and (d) in FIG. 4, the lengths of the four sides of the shielding plate on the upper side 31 are all shorter in length than those of the four sides on the lower side 32. As a result, as shown by (a) in FIG. 4, this shielding plate has a shape including steps 33 formed at the edge portions of four sides.

FIG. 5 shows another example in which four sides of a shielding plate have stepped halving joint structures. As understood from the cross-sectional views shown by (c) and (d) in FIG. 5, the upper side and the lower side of the shielding plate differ from each other in the lengths of the four sides. The two sides 31S among the four sides on the upper side 31 are shorter than the corresponding two sides on the lower side 32, while the other two sides 31L on the upper side are longer than the corresponding two sides on the lower side 32. As a result, as shown by (a) in FIG. 5, this shielding plate has a shape including steps 33 formed at the edge portions of four sides.

FIG. 6 shows an example in which three sides of a shielding plate have stepped halving joint structures. As understood from the cross-sectional views shown by (c) and (d) in FIG. 6, three sides among the four sides on the upper side of the shielding plate are shorter in length than the corresponding three sides on the lower side. As a result, as shown by (a) in FIG. 6, this shielding plate has a shape including steps formed at the edge portions of the three sides.

FIG. 7 shows an example in which two sides of a shielding plate have stepped halving joint structures. As understood from the cross-sectional views shown by (c) and (d) in FIG. 7, two sides among the four sides on the upper side 31 of the shielding plate are shorter in length than the corresponding two sides on the lower side 32. As a result, as shown by (a) in FIG. 7, this shielding plate has a shape including steps 33 formed at the edge portions of two sides.

FIG. 8 shows another example in which two sides of a shielding plate have stepped halving joint structures. As understood from the cross-sectional views shown by (c) and (d) in FIG. 8, the four sides on each of the upper side 31 and the lower side 32 of the shielding plate have the same length. However, two sides among the four sides are arranged at different positions from the corresponding two sides. As a result, as shown by (a) in FIG. 8, this shielding plate has a shape including steps 33 formed at the edge portions of two sides.

FIG. 9 shows an example in which one side of a shielding plate has a stepped halving joint structure. As understood from the cross-sectional views shown by (c) and (d) in FIG. 9, one side among the four sides on the upper side 31 of the shielding plate is shorter in length than the corresponding one side on the lower side 32. As a result, as shown by (a) in FIG. 9, this shielding plate has a shape including a step 33 formed at the edge portion of one side.

The above-described halving joint structures of shielding plates are not limited to stepped halving joint structures. A shielding plate having an inclined edge portion as shown by (b) in FIG. 3 may also similarly have a shape including an inclination formed at each edge portion of four sides, three sides, two sides, or one side.

Figure 16:
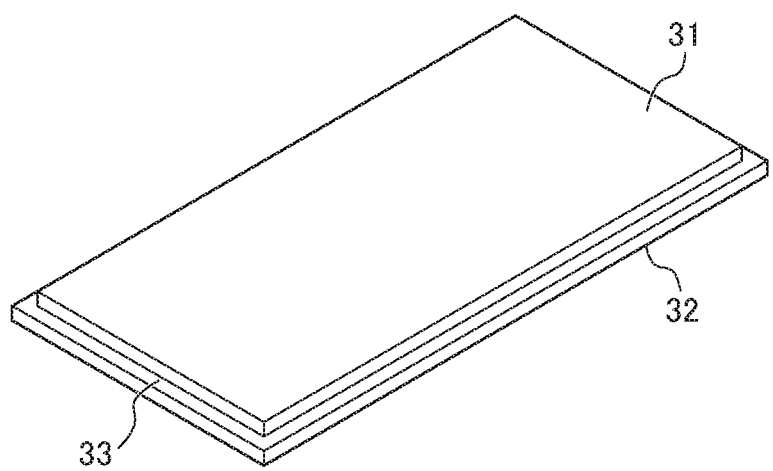
FIG. 16 is a view illustrating another exemplary form of an edge portion of a shielding plate having a halving joint structure.

The planar shapes of the shielding plates shown in FIGS. 4 to 9 are each a square, but the shape is not limited thereto and may be a rectangle as shown in FIG. 16.

The end faces of the shielding plates contacts closely with each other via the above-described halving joint structure to join the edge portions of the shielding plates. Accordingly, fixing the abutting portions of the shielding plates are stably fixed to each other, yielding an effect of enhanced mechanical strength.

A neutron beam may pass through the gap between the edge portions of the shielding plates. When the joining portion of the edge portions of the shielding plates is composed of an even and flat face, the neutron beam that has entered linearly from the outside may pass through the joining portion. In contrast, when the joining portion of the edge portion has a stepped or inclined halving joint structure as shown in (a) and (b) of FIG. 3 and FIGS. 4 to 9, a neutron beam entering linearly toward the gap between the edge portions of the shields is blocked by the shielding plate body, which results in an improved effect of preventing a neutron beam from entering.

(Face of Box-Type Structure)

The box-type structure has a plurality of faces, and at least one of the faces is preferably removable. The box-type structure is three-dimensionally configured and therefore has a plurality of outer faces. These faces have a removable structure. Accordingly, it is convenient for disassembling the box-type structure in, for example, preparation for an irradiation test or withdrawal after the test. In addition, the organism, i.e., an irradiation object, in the box-type structure can be easily put in and taken out.

The box-type structure can be provided with an opening portion in a part of the faces. Since the outside of the box-type structure is in an environment under irradiation with a neutron beam, it is possible to expose a part of the irradiation object to the outside through the opening portion and to irradiate the part exclusively. For example, in order to irradiate the leg of a mouse exclusively for a test with a neutron beam, it is possible to three-dimensionally cover the mouse body with the box-type structure and place only the leg of the mouse in the irradiation environment outside the box-type structure.

(Joining with Adhesive Tape)

The shielding plates can be joined with adhesive tape. The edge portions of the shielding plates are abutted against each other, and the shielding plate surfaces are then attached to adhesive tape to fix the shielding plates. Thus, a box-type structure can be assembled.

The box-type structure fixed with adhesive tape can be disassembled by peeling off the adhesive tape after being used in a necessary test or can be reassembled. The adhesive tape may be any known product without specific limitation. In order to minimize the radioactivation rate by irradiation with a neutron beam, it is preferable to select colorless transparent or translucent tape free from coloring components and inorganic fillers in the tape base. The adhesive component adhering to the tape base surface is not particularly limited and may be, for example, a rubber or acrylic adhesive agent. The material of the tape base is not particularly limited and may be, for example, cellophane or acetate.

(Joining with Adhesive)

The shielding plates can be joined by adhering the edge portions with an adhesive. The joining structure of the edge portions can be strengthened by applying adhesive to a face (end face) of the edge portions of the shielding plates and abutting the edge portions against each other. A part of the end faces of the shielding plates can be temporarily fixed with adhesive tape, and the part of the end faces can be permanently fixed with an adhesive afterwards. The temporarily fixed surface can be used as a removable opening surface.

The adhesive may be a known product without specific limitation. An adhesive such as an epoxy resin or a silicone resin can be used. Since epoxy resin has a low content of elements other than carbon, hydrogen, and oxygen, the radioactivation rate is low when irradiated with a neutron beam. Accordingly, it is suitable for use in medical fields such as radiotherapy. In addition, a two-liquid curing type epoxy resin is cured by mixing a main agent and a curing agent. Accordingly, when a powder is added, the main agent and the curing agent can be separately added to and kneaded with the powder and can be then mix for reaction and curing. Thus, the kneading time has a margin, and the workability is improved. It is possible to select an adhesive having appropriate working time, curing time and viscosity. If the viscosity is too low, the adhesive is apt to flow out of the applied gap, and the gap-filling property is reduced. Accordingly, it is preferable to use an adhesive having an appropriately high viscosity. A short curing time is problematic because the time margin for assembling shielding plates into a desired form is reduced. A long curing time is problematic because it requires an elongated time for maintaining the shape of the structure, and therefore, temporary fixing must be performed for a long time.

The adhesive used for joining shielding plates may contain a lithium fluoride powder in an amount of 30 wt % or more. Such an adhesive functions as a sealant filling the gap between the shielding plates, as well as glues the shielding plates together. An adhesive incorporates lithium fluoride containing 6Li, which has a neutron-shielding function, has the effect of preventing a neutron beam from entering through the gap between the shielding plates.

When the viscosity of the adhesive is low, the adhesive may contain a lithium fluoride powder in an amount of 40 wt % or more, 50 wt % or more, or 60 wt % or more for adjusting the viscosity to have appropriate application workability or enhanced neutron-shielding performance.

(Embodiment of Box-Type Structure)

The box-type structure of the present invention can be provided in various shapes and configurations by combining the above-described shielding plates. Exemplary forms thereof are shown in FIGS. 10 to 15.

(a) to (g) in FIG. 10 show embodiments related to the box-type structure. (a) in FIG. 10 is a perspective view, (b) in FIG. 10 is a front view, and (c) in FIG. 10 is a right-side view. (d) in FIG. 10 is a cross-sectional view along the line A-A, (e) in FIG. 10 is a cross-sectional view along the line B-B, and (f) in FIG. 10 is a cross-sectional view along the line C-C. (g) in FIG. 10 is a view illustrating the inside of the box-type structure when the upper shielding plate 46 is detached. As shown by (a) to (c) in FIG. 10, it is possible to provide a box-type structure composed of a combination of six shielding plates 41, 42, 43, 44, 45, and 46 that has a structure in which the shielding plates enclose internal space completely. The shielding plates 41, 42, 43, 44, 45, and 46 have a structure including the edge portions abutted and joined via the halving joint portions. On the inside of the box-type structure, the stepped halving joint structure has a concave on the inside, as shown by (b) in FIG. 10.

(a) to (h) in FIG. 11 show another embodiment related to the box-type structure. (a) in FIG. 11 is a perspective view, (b) in FIG. 11 is a perspective view from another direction, and (c) in FIG. 11 is a front view. (d) in FIG. 11 is a plan view, and (e) in FIG. 11 is a right-side view. (f) in FIG. 11 is a cross-sectional view along the line A-A, (g) in FIG. 11 is a cross-sectional view along the line B-B, and (h) in FIG. 11 is a cross-sectional view along the line C-C. As shown by (a) to (e) in FIG. 11, the box-type structure is composed of a combination of five shielding plates 41, 42, 43, 44, and 45. As shown by (f) to (h) in FIG. 11, these shielding plates are abutted and joined to each other via a halving joint structure formed at the edge portions. One opening is provided at the upper portion of the box-type structure to give a structure in which the halving joint portions at the edge portions of the shielding plates are arranged to protrude outwards along the periphery of the opening. Accordingly, covering the opening with another shielding plate makes it possible to give a joining structure including end faces contacting each other closely. In addition, it is possible to configure a rectangular parallelepiped box-type structure by combining the box-type structure with another box-type structure through connecting the openings to each other. A shielding plate may be attached to the opening so as to close a part of the opening.

Figure 12A:
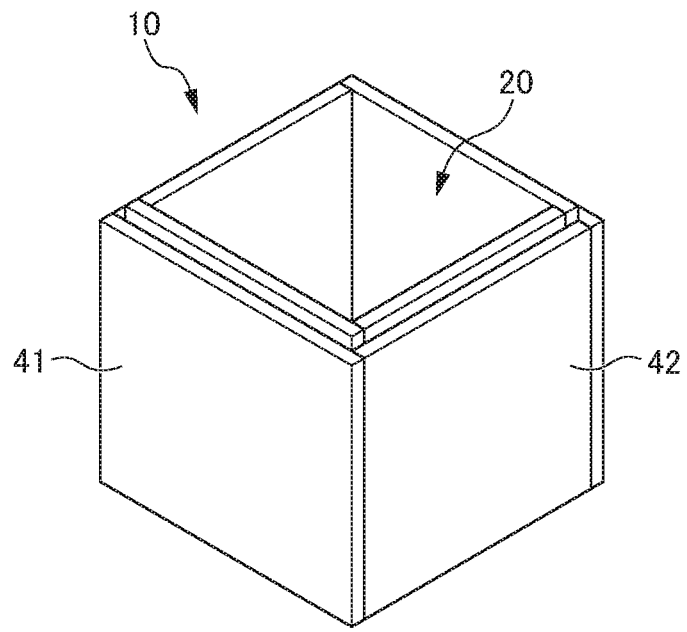
FIG. 12 includes views illustrating another embodiment related to the box-type structure. (a) is a perspective view, and (b) is a perspective view from another direction.
Figure 12B:
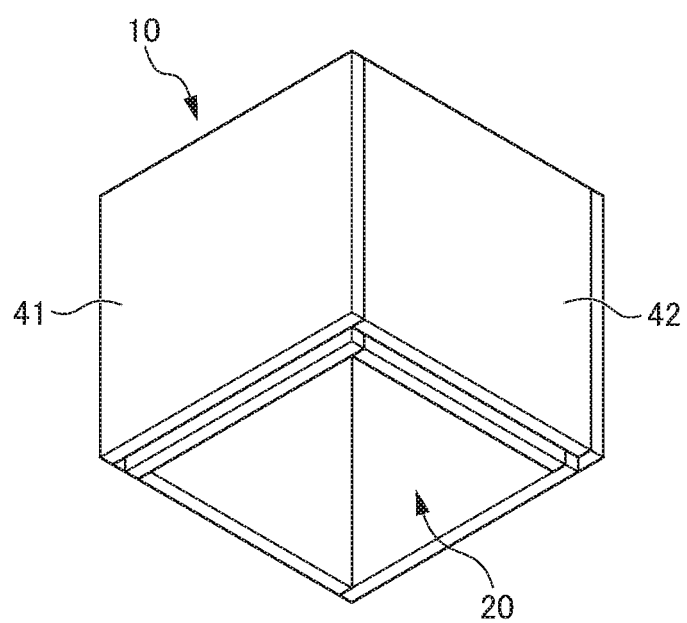

(a) and (b) in FIG. 12 show another embodiment related to the box-type structure. (a) in FIG. 12 is a perspective view, and (b) in FIG. 12 is a perspective view from another direction. As shown by (a) and (b) in FIG. 12, this is an example including an opening provided at each of the upper side and the lower side of the box-type opening portion. Similar to the box-type structure in FIG. 10, there is provided a structure in which the halving joint portions at the end portions of the shielding plates are arranged to protrude outward along the peripheries of the openings. Except the above, similar to the box-type structure in FIG. 10, the shielding plates 41, 42, 43, and 44 have a structure including the edge portions abutted and joined via the halving joint portions.

Figure 13A:
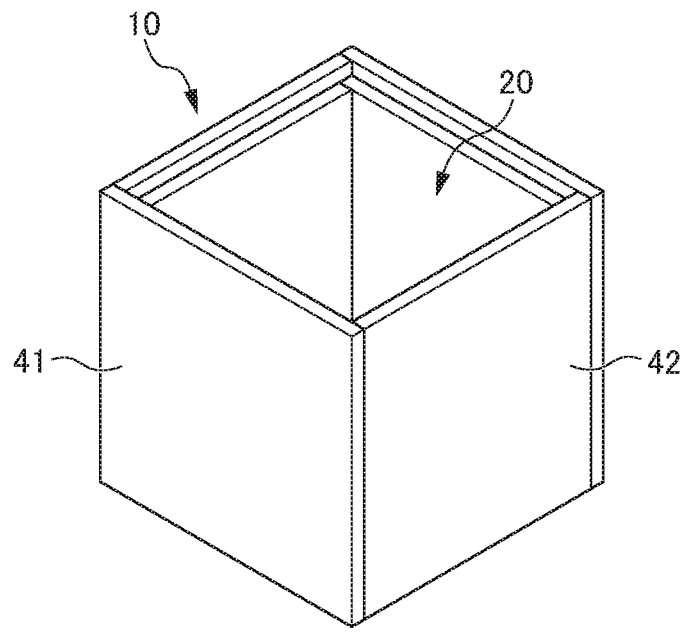
FIG. 13 includes views illustrating another embodiment related to the box-type structure. (a) is a perspective view, and (b) is a perspective view from another direction.
Figure 13B:
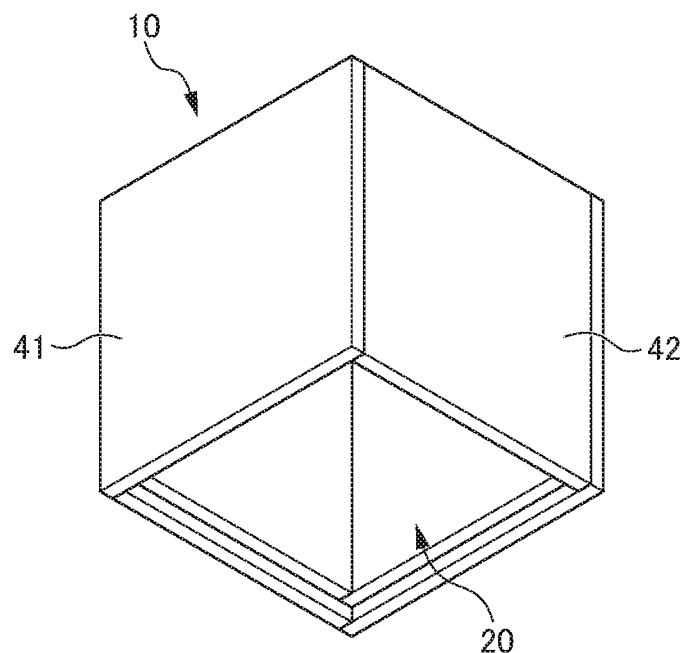

(a) and (b) in FIG. 13 are views illustrating another embodiment related to the box-type structure. (a) in FIG. 13 is a perspective view, and (b) in FIG. 13 is a perspective view from another direction. As shown by (a) and (b) in FIG. 13, this is an example including an opening provided at each of the upper side and the lower side of the box-type opening portion. Similar to the box-type structure in FIG. 11, there is provided a structure in which the halving joint portions at the end portions of the shielding plates are arranged to face inward along the peripheries of the openings. Except for the above, similar to the box-type structure in FIG. 10, the shielding plates 41, 42, 43, and 44 have a structure including the edge portions abutted and joined via the halving joint portions.

Figure 14A:
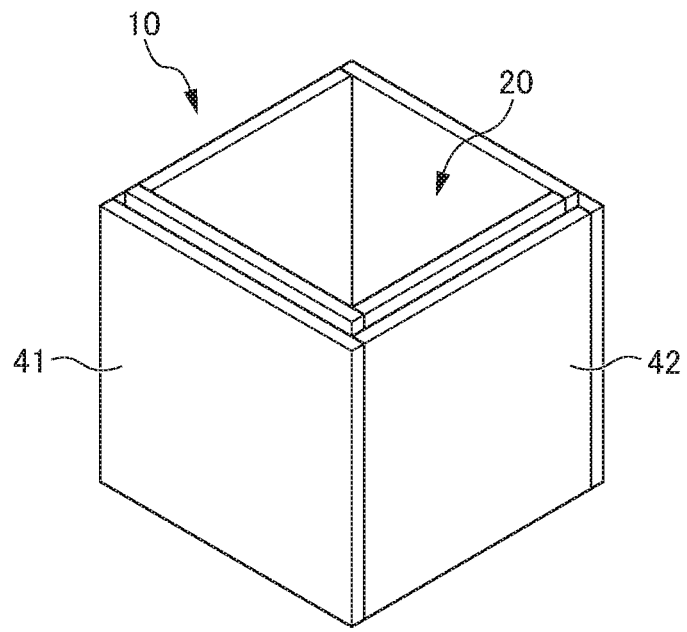
FIG. 14 includes views illustrating another embodiment related to the box-type structure. (a) is a perspective view, and (b) is a perspective view from another direction.
Figure 14B:
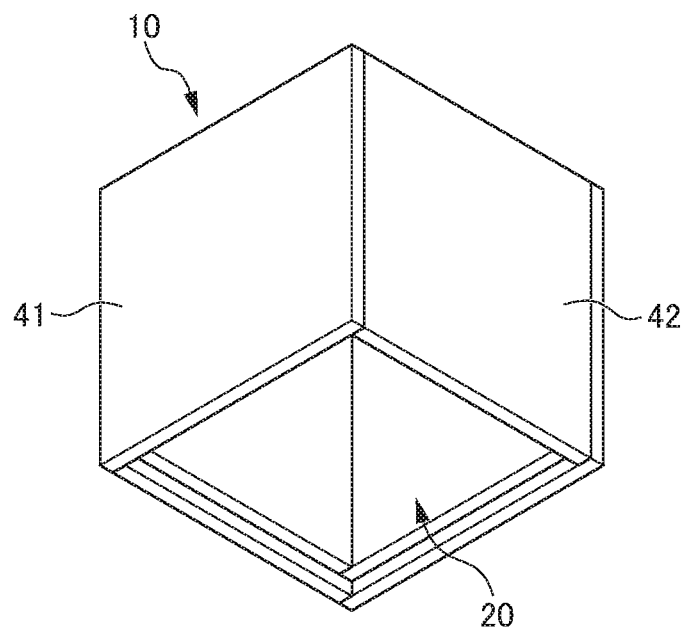

(a) and (b) in FIG. 14 show another embodiment related to the box-type structure. (a) in FIG. 14 is a perspective view, and (b) in FIG. 14 is a perspective view from another direction. As shown by (a) and (b) in FIG. 14, this is an example including an opening provided at each of the upper side and the lower side of the box-type opening portion. Similar to the box-type structure in FIG. 10, there is provided a structure in which the halving joint portions at the edge portions of the shielding plates are arranged to protrude outward along the periphery of the opening at the upper side. Similar to the box-type structure in FIG. 11, there is provided a structure in which the halving joint portions at the edge portions of the shielding plates are arranged to face inward along the periphery of the opening at the lower side. Except for the above, similar to the box-type structure in FIG. 10, the shielding plates 41, 42, 43, and 44 have a structure including the edge portions abutted and joined via the halving joint portions.

Figure 15:
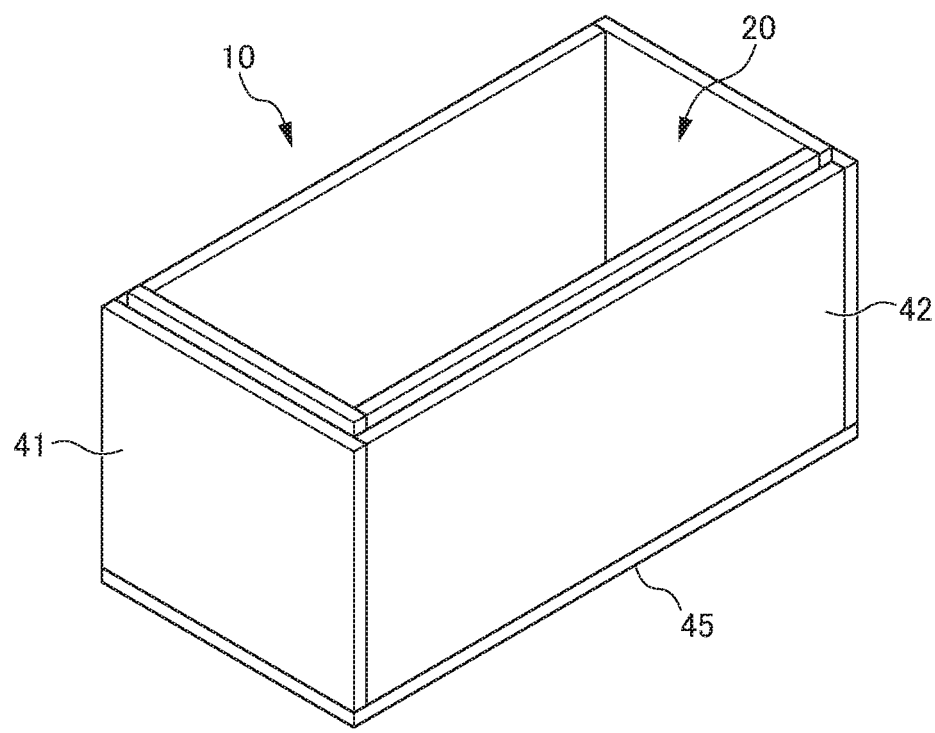
FIG. 15 is a perspective view illustrating another embodiment related to the box-type structure.

The shielding plates shown in FIGS. 10 to 14 each have a square plane shape, but the shape is not limited thereto and may be a rectangle as shown in FIG. 15.

(Regarding Lithium Fluoride Powder Material and a Lithium Fluoride Sintered Body)

Regarding a material containing lithium fluoride (LiF), Li includes two stable isotopes $^6$Li and $^7$Li. The natural abundance ratios of $^7$Li and $^6$Li are 92.5 atom % and 7.5 atom %, respectively. Since $^6$Li contributes to the shielding of a neutron beam, the neutron beam can be more efficiently shielded by using $^6$LiF containing $^6$Li. The shielding plate made of a lithium fluoride-containing material is preferably a lithium fluoride sintered body prepared by shaping and sintering a lithium fluoride powder to obtain an edge portion structure having a predetermined shape. For the material of the shielding plate according to the present embodiment, the content of $^6$Li can be adjusted according to the necessary neutron-shielding performance. For example, when high neutron shielding performance is required, it is possible to select a lithium fluoride powder material having a $^6$Li content of 95 atom % and a LiF purity of 99% or more. Alternatively, it is also possible to use lithium fluoride having an appropriately adjusted content ratio of $^6$Li and $^7$Li.

A lithium fluoride sintered body including $^6$LiF can be obtained without adding a sintering agent or other inorganic compound to form a composite material. Accordingly, the shielding plate made of lithium fluoride according to the present embodiment can have excellent neutron-shielding performance due to the high purity of the lithium fluoride itself.

For the lithium fluoride-containing material according to the present embodiment, the purity of LiF is preferably 99 wt % or more. If the shield material contains a large amount of impurities, such as metal components (elements), the impurities irradiated with a neutron beam might be radioactivated to emit gamma rays. LiF itself is not radioactivated even if irradiated with a neutron beam. Accordingly, regarding the lithium fluoride-containing material according to the present embodiment, if the purity of the lithium fluoride itself is low or a sintering agent or other inorganic compound, i.e., a composite material, is mixed, such impurities or mixed components may be radioactivated and emit gamma rays. Thus, the use of lithium fluoride having a high purity is desirable.

Examples of methods for manufacturing a lithium fluoride product include a single crystal growth method, a solidifying method from a melt, and a sintering method. However, the sintering method is preferable because this method makes it possible to supply a stable-quality product at a low cost.

The single crystal growth method requires high control accuracy during manufacturing, resulting in low quality stability and a significantly high product price. In addition, the resulting single-crystal body has problems such as a high cost for processing into a predetermined shape, cleavability, and the easy occurrence of cracks during processing. The solidifying method from a melt requires strict temperature control during cooling and requires cooling for a long time, resulting in difficulty in obtaining a solid substance having a relatively large size and is homogeneous and defect-fee throughout the substance.

The sintered body of lithium fluoride (hereinafter may be also referred to as "LiF sintered body") preferably has a relative density of 86% or more and 92% or less. In the present embodiment, the relative density is a value obtained by dividing the density of a sintered body by the theoretical density of LiF (2.64 g/cm$^3$) and multiplying the result by 100. The lithium fluoride sintered body having a relative density within the above range has the advantage that swelling and the occurrence of voids and cracks during sintering are suppressed to provide excellent machinability. The LiF sintered body is not highly-densified, resulting in the advantage of excellent machinability.

If the relative density is too low, there is a risk that the LiF sintered body does not have sufficient neutron-shielding performance. In addition, if the relative density is too low, there is a concern that the ratio of voids inside the sintered body is high, resulting in an inferior mechanical strength.

In contrast, if the relative density is too high, the LiF sintered body has sufficient neutron-shielding performance. However, there is a concern that the sintered body is highly densified such that the processing of the sintered body may cause cracks or the like due to a released residual stress inside the material.

The thickness of the LiF sintered body is not particularly limited as long as a neutron beam can be suitably blocked. Specifically, the thickness of the LiF sintered body is preferably 2 mm or more and more preferably 3 mm or more from the viewpoint of the mechanical strength of the sintered body and the workability during the halving joint processing.

The upper limit of the thickness of the LiF sintered body is not particularly limited. From the viewpoint of reducing the size and weight of the shielding plate, a thinner LiF sintered body is preferred within a range capable of suitably shielding a neutron beam. Specifically, the thickness of the LiF sintered body is preferably 8 mm or less and more preferably 5 mm or less.

(Method for Manufacturing LiF Sintered Body)

The method for manufacturing the LiF sintered body according to the present embodiment includes a pressing step of pressing a LiF composition containing a LiF powder and an organic shaping agent to prepare a pressed body, and a firing step of firing the pressed body at 630° C. or more and 830° C. or less. Prior to the firing step, for example, a preliminary firing step for degreasing the organic shaping agent may be performed.

EXAMPLES

The present invention will now be described in more detail using examples. The present invention is not limited to these descriptions.

(Manufacturing of Box-Type Structure)

Base plates of a lithium fluoride (LiF) sintered body having a length of 80 mm, a width of 40 mm, and a thickness of 5 mm were produced. This sintered body had a relative density within a range of 88.9% to 91.3%. A shielding plate 1A and a shielding plate 2A each having a halving joint structure with a predetermined shape were produced by performing halving joint processing for forming a step having a length of about 2.5 mm along the peripheries of the base plates. The shielding plates 1A and 2A were each provided with a step at each of three peripheral edges. In addition, base plates having a length of 80 mm, a width of 40 mm, and a thickness of 5 mm were produced and subjected to halving joint processing for forming a step having a length of about 2.5 mm at each of the four peripheral edges to produce shielding plates 3A and 3B. Similarly, a base plate having a length of 80 mm, a width of 45 mm, and a thickness of 5 mm was produced and subjected to halving joint processing for forming a step having a length of about 2.5 mm at each of the four edges to produce a shielding plate 4A. Furthermore, a base plate having a length of 80 mm, a width of 25 mm, and a thickness of 5 mm was similarly produced and subjected to halving joint processing for forming a step having a length of about 2.5 mm at each of the three edges to produce a shielding plate 4B.

Figure 18:
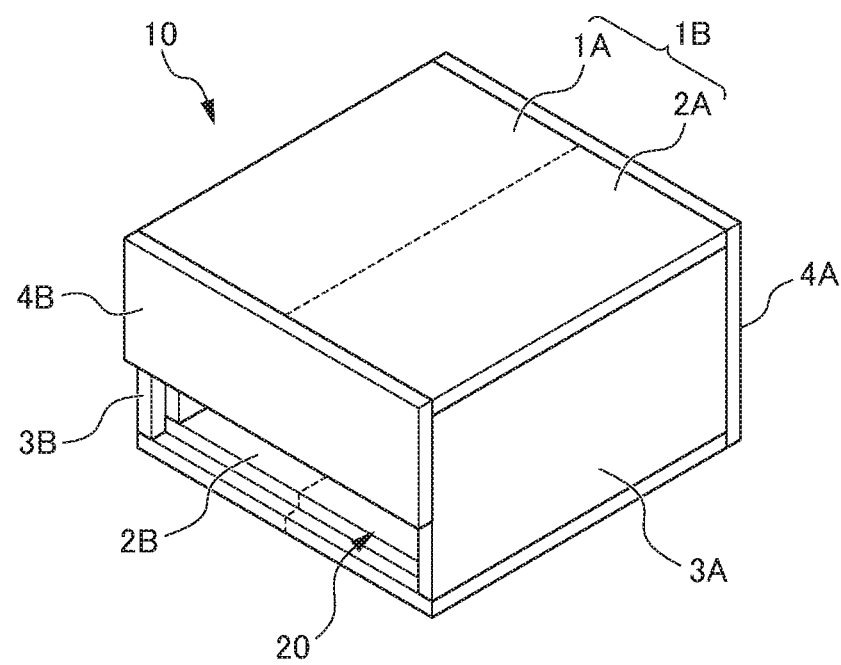
FIG. 18 is a view for explaining a box-type structure of an Example.

Subsequently, the shielding plate 1A and the shielding plate 2A were abutted against each other such that two were joined to each other at the edge portions of side faces where no halving joint was provided in the longitudinal direction, to produce a shielding plate 1B and a shielding plate 2B each having a length of 80 mm and a width of 80 mm. In the abutting and joining, a two-liquid curing type epoxy adhesive Araldite (registered trademark) Rapid (manufactured by Huntsman Japan KK) was used. 100 mg of a lithium fluoride powder having a 6Li content of 95 atm % and a LiF purity of 99% or more was added to each of 100 mg of the main agent and 100 mg of the curing agent, followed by uniformly mixing to prepare a main agent mixture and a curing agent mixture each containing 50 wt % of the lithium fluoride powder. Subsequently, both agents were uniformly mixed to make an adhesive containing lithium fluoride in an amount of 50 wt % of the whole adhesive. A part thereof was applied to the edge portions of the shielding plates and cured to fix the plates. These shielding plates 1B, 2B, 3A, 3B, 4A, and 4B were combined to assemble a box-type structure as shown in FIG. 18.

EXPLANATION OF REFERENCE NUMERALS

1, 2, 3, 4, 5 shielding plate
10 box-type structure
20 opening
21 joining structure
22, 23, 24, 25, 26, 27 shielding plate
31 upper side of shielding plate
32 lower side of shielding plate
33 step
41, 42, 43, 44, 45, 46 shielding plate
51, 52, 53, 54, 55, 56 shielding plate

What is claimed is:

1. A box-type structure comprising shielding plates made of a sintered body of lithium fluoride, having neutron-shielding performance, wherein edge portions of the shielding plates are abutted and joined to each other.

2. The box-type structure according to claim 1, wherein the edge portions of the shielding plates have a halving joint structure, and the halving joint structure has a stepped or inclined cutout shape.

3. The box-type structure according to claim 1, wherein the box-type structure has a plurality of faces, and at least one of the faces is removable.

4. The box-type structure according to claim 1, wherein a part of the faces of the box-type structure has an opening portion.

5. The box-type structure according to claim 1, wherein the shielding plates are joined with adhesive tape.

6. The box-type structure according to claim 1, wherein the edge portions of the shielding plates are joined via an adhesive.

* * * * *